United States Patent [19]

Bru-Magniez et al.

[11] Patent Number: 5,364,860

[45] Date of Patent: Nov. 15, 1994

[54] NAPHTHYRIDINE COMPOUNDS WHICH INHIBIT TYROSINE KINASE AND THEIR PHARMACEUTICAL COMPOSITIONS

[75] Inventors: Nicole Bru-Magniez, Paris; Michéle Launay, Rueil-Malmaison; Jean-Marie Teulon, La Celle Saint Cloud, all of France

[73] Assignee: Laboratoires UPSA, Agen, France

[21] Appl. No.: 97,239

[22] Filed: Jul. 27, 1993

[30] Foreign Application Priority Data

Jun. 25, 1993 [FR] France ............... 93 07746

[51] Int. Cl.$^5$ .................. A61K 31/44; C07D 471/02
[52] U.S. Cl. ............................. 514/300; 546/122
[58] Field of Search .............. 546/122; 514/300

[56] References Cited

U.S. PATENT DOCUMENTS 4,622,328 11/1986 Teulon ............. 546/122
4,786,642 11/1988 Teulon ............. 546/122

FOREIGN PATENT DOCUMENTS 0267691 5/1988 European Pat. Off. ....... 546/122
46-10560 3/1971 Japan ........................... 546/122

Primary Examiner—C. Warren Ivy
Assistant Examiner—Zinna N. Davis
Attorney, Agent, or Firm—Armstrong, Westerman, Hattori, McLeland & Naughton

[57] ABSTRACT

The present invention relates to the derivatives of the formula

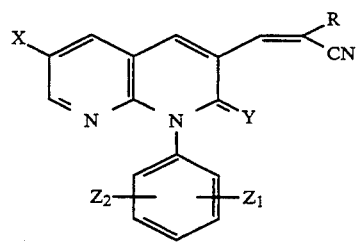

and their addition salts, and to their use in therapeutics, especially as drugs having antiproliferative properties and affording an effective treatment for diseases such as atherosclerosis, restenosis phenomena or any other pathological condition due to cell proliferation.

11 Claims, No Drawings

NAPHTHYRIDINE COMPOUNDS WHICH INHIBIT TYROSINE KINASE AND THEIR PHARMACEUTICAL COMPOSITIONS

The present invention relates, by way of novel products, to the naphthyridine derivatives of general formula (I) below and their addition salts, in particular the pharmaceutically acceptable addition salts.

The compounds of the invention, may be used in the treatment of atherosclerosis, restenosis phenomena or any other pathological condition due to cell proliferation in mammals and especially in man.

The present invention further relates to the method of preparing said products and to their applications in therapeutics.

These naphthyridine derivatives have general formula (I):

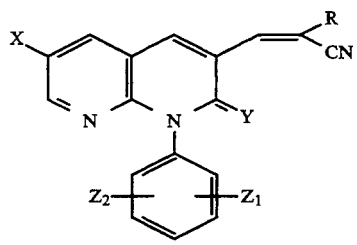

Formula (I)

in which:
X is:
— the hydrogen atom,
— a halogen atom,
— an OH radical or
— a lower O-alkyl radical having 1 to 6 carbon atoms;
Y is:
— the oxygen atom,
— the sulfur atom or
— an NH group;
$Z_1$ and $Z_2$ are independently:
— the hydrogen atom,
— a lower alkyl radical having 1 to 6 carbon atoms,
— a halogen atom,
— a trifluoromethyl radical,
— an OH radical,
— a lower O-alkyl radical having 1 to 6 carbon atoms,
— a lower S-alkyl radical having 1 to 6 carbon atoms,
— an $NO_2$ radical or
— a CN radical,
or $Z_1$ and $Z_2$ together form a methylenedioxy group; and
R is:
— a pyridine ring,
— an imidazole ring,
— an indole ring,
— a group —$CONH_2$ or —$CSNH_2$,
— a group

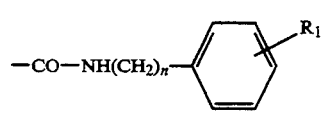

in which n is an integer from 0 to 5 and $R_1$ is the hydrogen atom or a halogen atom, or
— a group $COOR_2$, $R_2$ being a lower alkyl radical having 1 to 6 carbon atoms.

In the description and the claims, lower alkyl is understood as meaning a linear or branched hydrocarbon chain having from 1 to 6 carbon atoms. A lower alkyl radical is for example a methyl, ethyl, propyl, isopropyl, butyl, isobutyl, tert-butyl, pentyl, isopentyl, hexyl or isohexyl radical.

Halogen is understood as meaning a chlorine, bromine, iodine or fluorine atom.

Advantageously, within the framework of the present invention, a compound of formula (I) will be used in which at least one of the following conditions is satisfied:
— X is the hydrogen atom,
— Y is the oxygen atom,
— Y is the sulfur atom,
— $Z_1$ is the hydrogen atom,
— $Z_1$ is the chlorine atom,
— $Z_2$ is a methoxy group,
— $Z_2$ is the chlorine atom, and
— R is a pyridine ring.

The particularly preferred compounds of the invention are selected from the products of the formulae:

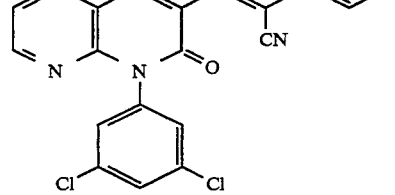

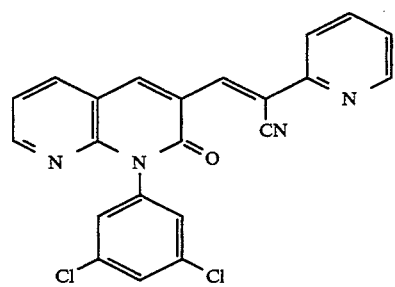

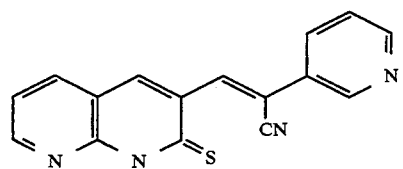

-continued

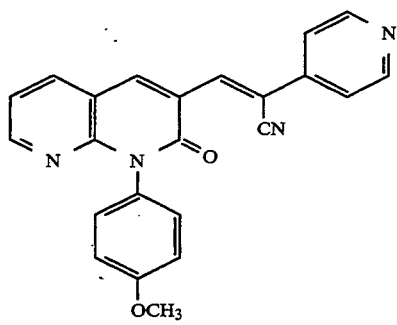

According to the invention, the compounds of formula (I) may be synthesized in the following manner:

The reaction of a 2-chloronicotinic acid of formula (II):

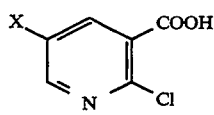

Formula (II)

in which X is as defined above, with an aniline of formula (III):

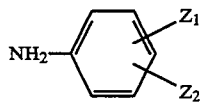

Formula (III)

in which $Z_1$ and $Z_2$ are as defined above, by heating in a solvent such as, for example, toluene or xylene, will give the 2-anilinonicotinic acids of formula (IV):

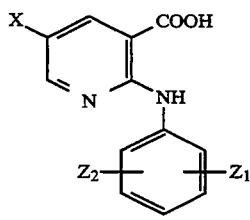

Formula (IV)

in which X, $Z_1$ and $Z_2$ are as defined above, according to a method known in the literature: U.S. Pat. No. 3,415,834; C. Hoffmann, A. Faure, Bull. Soc. Chim. France 1966, 2316.

The reduction of an acid of formula (IV) or one of its esters, for example the methyl or ethyl ester, with a conventional reducing agent such as, for example, lithium aluminum hydride, in an organic solvent such as, for example, tetrahydrofuran or ethyl ether, will give the alcohols of formula (V):

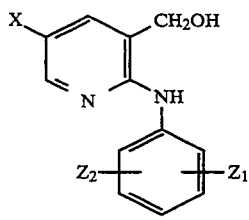

Formula (V)

in which X, $Z_1$ and $Z_2$ are as defined above.

In the case where the phenyl ring carries a substituent sensitive to certain reducing agents, such as nitro or cyano, for example, the reducing agent chosen for reducing the ester will be one which does not affect this substituent, for example lithium borohydride prepared in situ from potassium borohydride and lithium chloride in tetrahydrofuran, or else sodium borohydride in dioxane.

The oxidation of an alcohol of formula (V) with a mild oxidizing agent such as, for example, $MnO_2$, in an organic solvent such as dichloromethane, chloroform, toluene or xylene, at a temperature between 20° and 80° C., will give the nicotinaldehydes of formula (VI):

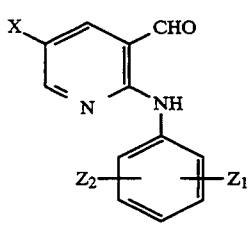

Formula (VI)

in which X, $Z_1$ and $Z_2$ are as defined above.

If X in formula (VI) is the hydrogen atom, reaction with chlorine, bromine or iodine chloride, for example, in a solvent such as dichloromethane, chloroform, dichloroethane or acetic acid, will give the derivatives in which X is a halogen atom; these derivatives may react with a sodium or potassium alcoholate to give the derivatives in which X is a lower O-alkyl radical having 1 to 6 carbon atoms, which may be converted to derivatives in which X is an OH radical by reaction with hydrobromic acid or pyridine hydrochloride according to methods known to those skilled in the art.

The reaction of the aldehydes of formula (VI) with an alkyl dialkoxypropionate of formula (VII):

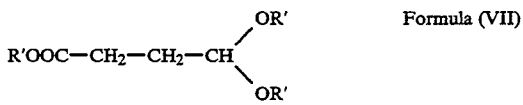

Formula (VII)

in which R' is a lower alkyl radical having 1 to 6 carbon atoms, optimally the methyl radical, or else with a dialkoxypropionitrile of formula (VII'):

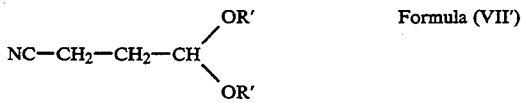

Formula (VII')

in which R' is as defined in formula (VII), in tetrahydrofuran, in the presence of a sodium or potassium alcoholate, will give the derivatives of formula (VIII):

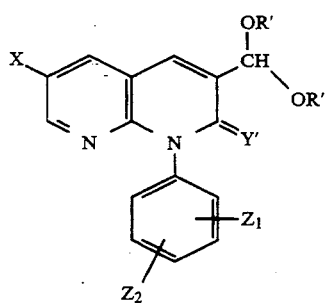

Formula (VIII)

in which X, $Z_1$, $Z_2$ and R' are as defined above and Y' is an oxygen atom in the case where the reaction has been carried out with the compound of formula (VII), or an NH group in the case where the reaction has been carried out with the compound of formula (VII').

The dialkylacetal derivatives of formula (VIII) will be hydrolyzed, for example by reaction with hydrochloric acid in a solvent such as tetrahydrofuran, to give the aldehydes of formula (IX):

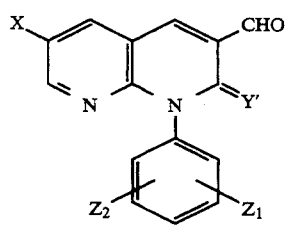

Formula (IX)

in which X, $Z_1$, $Z_2$ and Y' are as defined above.

The reaction of the aldehydes of formula (IX) with an activated methylene of formula (X):

R—CH$_2$—CN

Formula (X)

in which R is as defined in formula (I), according to the conventional methods of the Knoevenagel reaction, for example by heating in an alcohol such as methanol or ethanol, in the presence of piperidine or a sodium or potassium alcoholate, will give the compounds of formula (XI):

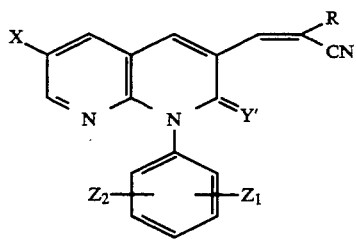

Formula (XI)

in which X, R, Y', $Z_1$ and $Z_2$ are as defined above.

By treatment with P$_4$S$_{10}$ in xylene under reflux, the derivatives of formula (XI) in which Y' is the oxygen atom may give the derivatives of formula (I) in which Y is the sulfur atom.

In certain cases, the reaction of the aldehyde of formula (IX) with the nitrile of formula (X) will give the hydroxylated compounds of formula (XII):

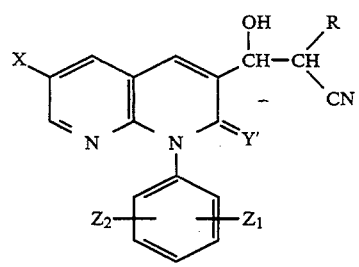

Formula (XII)

in which X, Y', $Z_1$ and $Z_2$ are as defined above, instead of giving the ethylenic compounds of formula (XI) directly.

In this case, the derivatives of formula (XII) will be dehydrated to compounds of formula (XI) by methods known to those skilled in the art, for example by reaction with trifluoroacetic anhydride and trifluoroacetic acid or else with paratoluenesulfonic acid in a solvent such as dichloromethane or chloroform, or else toluene or xylene, at a temperature between 20° and 130° C.

The compounds of formula (I) as defined above, and their addition salts, in particular the pharmaceutically acceptable addition salts, possess a very good antiproliferative activity.

These properties justify their application in therapeutics and the invention further relates, by way of drugs, to the products as defined by formula (I) above, and their addition salts, in particular the pharmaceutically acceptable addition salts.

Addition salts of some of the compounds of formula (I) can be obtained by reacting these compounds with a mineral or organic acid by a method known per se. Among the acids which can be used for this purpose, there may be mentioned hydrochloric, hydrobromic, sulfuric, phosphoric, toluene-4-sulfonic, methanesulfonic, cyclohexylsulfamic, oxalic, succinic, formic, fumaric, maleic, citric, aspartic, cinnamic, lactic, glutamic, N-acetylaspartic, N-acetylglutamic, ascorbic, malic, benzoic, nicotinic and acetic acids.

Thus the invention also covers a pharmaceutical composition which comprises a pharmaceutically effective amount of at least one compound of formula (I) as defined above, or one of its pharmaceutically acceptable addition salts, which may or may not be incorporated in a pharmaceutically acceptable excipient, vehicle or carrier.

These compositions can be administered by the buccal, rectal, parenteral, transdermal or ocular route.

These compositions can be solid or liquid and can be presented in the pharmaceutical forms commonly used in human medicine, such as, for example, simple or coated tablets, gelatin capsules, granules, suppositories, injectable preparations, transdermal systems and eye lotions. They are prepared by the customary methods. The active principle, which consists of a pharmaceutically effective amount of at least one compound of formula (I) as defined above, or one of its pharmaceutically acceptable addition salts, can be incorporated therein with excipients normally employed in these pharmaceutical compositions, such as talc, gum arabic, lactose, starch, magnesium stearate, polyvidone, cellulose derivatives, cacao butter, semisynthetic glycerides, aqueous or non-aqueous vehicles, fatty substances of animal or vegetable origin, glycols, various wetting agents, dispersants or emulsifiers, silicone gels, certain polymers or copolymers, preservatives, flavorings and colors.

The invention also covers an antiproliferative pharmaceutical composition affording especially a favorable treatment for any pathological condition due to cell proliferation, which comprises a pharmaceutically effective amount of at least one compound of formula (I) given above, or one of its pharmaceutically acceptable addition salts, which may or may not be incorporated in a pharmaceutically acceptable excipient, vehicle or carrier.

The invention also covers a method of preparing a pharmaceutical composition, which comprises incorporating a pharmaceutically effective amount of at least one compound of formula (I) as defined above, or one of its pharmaceutically acceptable addition salts, into a pharmaceutically acceptable excipient, vehicle or carrier. In one embodiment, a pharmaceutical composition with antiproliferative activity is prepared which affords especially a favorable treatment for atherosclerosis, restenosis phenomena or any other pathological condition due to cell proliferation.

In one variant, a composition is formulated as gelatin capsules or tablets containing from 1 mg to 1000 mg of active ingredient, or as injectable preparations containing from 0.1 mg to 500 mg of active ingredient. Formulations as suppositories, ointments, creams, gels, aerosol preparations or eye lotions may also be used.

The invention also covers a method of therapeutic treatment for mammals, which comprises administering to this mammal a therapeutically effective amount of at least one compound of formula (I) as defined above, or one of its pharmaceutically acceptable addition salts. In one variant of this method of treatment, the compound of formula (I), either by itself or in association with a pharmaceutically acceptable excipient, is formulated as gelatin capsules or tablets containing from 1 mg to 1000 mg of active ingredient for oral administration, or as injectable preparations containing from 0.1 to 500 mg of active ingredient, or else as suppositories, ointments, creams, gels, aerosol preparations or eye lotions.

In human and animal therapeutics, the compounds of formula (I) and their salts can be administered by themselves or in association with a physiologically acceptable excipient, in any form, in particular in the form of gelatin capsules or tablets for oral administration or in the form of an injectable solution for parenteral administration. Other forms of administration, such as suppositories, ointments, creams, gels, aerosol preparations or eye lotions, can be envisaged.

As will be clearly apparent from the pharmacological tests given at the end of the description, the compounds according to the invention can be administered in human therapeutics for the above-mentioned indications, orally in the form of tablets or gelatin capsules containing from 1 mg to 1000 mg of active ingredient, or parenterally in the form of injectable preparations containing from 0.1 mg to 500 mg of active ingredient, in one or more daily dosage units for an adult with an average weight of 60 to 70 kg.

In animal therapeutics, the daily dose which can be used is between 0.1 and 100 mg per kg.

Further characteristics and advantages of the invention will be understood more clearly from the following description of some Examples, which in no way imply a limitation but are given by way of illustration.

EXAMPLE 1

2-(3-Trifluoromethylphenyl)amino-3-hydroxymethylpyridine

Formula (V): $X = Z_2 = H$, $Z_1 = 3-CF_3$

A solution of 200 g of 2-(3-trifluoromethylphenyl)aminonicotinic acid in 500 ml of anhydrous tetrahydrofuran is added dropwise to a suspension of 52 g of lithium aluminum hydride in 1000 ml of anhydrous ethyl ether. When the addition is complete, the reaction mixture is refluxed for 3 h. After cooling, the excess hydride is destroyed by the addition of ethyl acetate followed by a saturated aqueous solution of sodium sulfate. The precipitate formed is filtered off and washed with ether. The combined filtrates are evaporated under vacuum and 185.2 g of 2-(3-trifluoromethylphenyl)amino-3-hydroxymethylpyridine are recovered in the form of crystals melting at 103°–105° C.

The derivatives of Examples 2 to 11 are prepared by this method.

EXAMPLE 2

2-Phenylamino-3-hydroxymethylpyridine

Formula (V): $X = Z_1 = Z_2 = H$

Oil; yield 95%.

EXAMPLE 3

2-(4-Fluorophenyl)amino-3-hydroxymethylpyridine

Formula (V): $X = Z_2 = H$, $Z_1 = 4-F$

Crystals; m.p. = 89°–90° C.; yield 88%.

EXAMPLE 4

2-(3-Methylthiophenyl)amino-3-hydroxymethylpyridine

Formula (V): $X = Z_2 = H$, $Z_1 = 3-SCH_3$

Oil; yield 95%.

EXAMPLE 5

2-(2,5-Difluorophenyl)amino-3-hydroxymethylpyridine

Formula (V): $X = H$, $Z_1 = 2-F$, $Z_2 = 5-F$

Crystals; m.p. = 71°–74° C.; yield 98%.

EXAMPLE 6

2-(3-Methoxyphenyl)amino-3-hydroxymethylpyridine

Formula (V): $X = Z_2 = H$, $Z_1 = 3-OCH_3$

Crystals; m.p. = 94° 95° C.; yield 98%.

EXAMPLE 7

2-(3-Chlorophenyl)amino-3-hydroxymethylpyridine

Formula (V): $X = Z_2 = H$, $Z_1 = 3-Cl$

Crystals; m.p. = 114°–115° C.; yield 94%.

EXAMPLE 8

2-(4-Chlorophenyl)amino-3-hydroxymethylpyridine

Formula (V): $X = Z_2 = H$, $Z_1 = 4-Cl$

Crystals; m.p. = 124°–126° C.; yield 95%.

EXAMPLE 9

2-(3,5-Dichlorophenyl)amino-3-hydroxymethylpyridine

Formula (V): $X = H$, $Z_1 = 3-Cl$, $Z_2 = 5-Cl$

Crystals; m.p. = 149° C.; yield 90%.

EXAMPLE 10

2-(4-Methoxyphenyl)amino-3-hydroxymethylpyridine

Formula (V): $X=Z_2=H$, $Z_1=4$—$OCH_3$
Crystals; m.p.=93° C.; yield 86.5%.

EXAMPLE 11

2-(3-Methylphenyl)amino-3-hydroxymethylpyridine

Formula (V): $X=Z_2=H$, $Z_1=3$—$CH_3$
Oil; yield 92%.

EXAMPLE 12

2-(3-Cyanophenyl)amino-3-hydroxymethylpyridine

Formula (V): $X=Z_2=H$, $Z_1=3$—CN 8 g of lithium chloride are added in small portions, with stirring, to a solution of 39.3 g of methyl 2-(3-cyanophenyl)aminonicotinate in 600 ml of tetrahydrofuran containing 10 g of potassium borohydride. When the addition is complete, the mixture is refluxed for 4 h and then concentrated under vacuum. After the addition of water and ice to the residue obtained, extraction is carried out with ether and the ether phase is washed with water and then dried over sodium sulfate.

After evaporation of the ether, 31.6 g of 2-(3-cyanophenyl)amino-3-hydroxymethylpyridine are obtained in the form of crystals melting at 126° C.

The derivatives of Examples 13 to 15 are prepared by this method.

EXAMPLE 13

2-(3-Nitrophenyl)amino-3-hydroxymethylpyridine

Formula (V): $X=Z_2=H$, $Z_1=3$—$NO_2$
Crystals; m.p.=150°-155° C.; yield 84%.

EXAMPLE 14

2-(3-Cyano-4-chlorophenyl)amino-3-hydroxymethylpyridine

Formula (V): $X=H$, $Z_1=3$—CN, $Z_2=4$—Cl
Crystals; m.p.=147° C.; yield 90%.

EXAMPLE 15

2-(3-Cyano-4-fluorophenyl)amino-3-hydroxymethylpyridine

Formula (V): $X=H$, $Z_1=3$—CN, $Z_2=4$—F
Crystals; m.p.=126° C.; yield 90%.

EXAMPLE 16

2-(3-Trifluoromethylphenyl)aminonicotinaldehyde

Formula (VI): $X=Z_2=H$, $Z_1=3$—$CF_3$ 690 g of $MnO_2$ are added in small portions to a solution of 185 g of 2-(3-trifluoromethylphenyl)amino-3-hydroxymethylpyridine, prepared in Example 1, in 2300 ml of chloroform. When the addition is complete, the mixture is stirred at room temperature for 6 h. The reaction medium is then filtered on Célite and the filtrate is evaporated to dryness. The resulting crystals, weighing 175 g, are recrystallized from heptane. 160 g of 2-(3-trifluoromethylphenyl)aminonicotinaldehyde are thus recovered in the form of crystals melting at 80°-81° C.

The derivatives of Examples 17 to 30 are prepared by this method.

EXAMPLE 17

2-Phenylaminonicotinaldehyde

Formula (VI): $X=Z_1=Z_2=H$
Crystals (isopropyl ether); m.p.=77°-78° C.; yield 80%.

EXAMPLE 18

2-(3-Cyanophenyl)aminonicotinaldehyde

Formula (VI): $X=Z_2=H$, $Z_1=3$—CN
Crystals (acetonitrile); m.p.=153°-154° C.; yield 60%.

EXAMPLE 19

2-(4-Fluorophenyl)aminonicotinaldehyde

Formula (VI): $X=Z_2=H$, $Z_1=4$—F
Crystals; m.p.=67°-68° C.; yield 71%.

EXAMPLE 20

2-(3-Methylthiophenyl)aminonicotinaldehyde

Formula (VI): $X=Z_2=H$, $Z_1=3$—$SCH_3$
Crystals; m.p.=63°-64° C.; yield 70%.

EXAMPLE 21

2-(2,5-Difluorophenyl)aminonicotinaldehyde

Formula (VI): $X=H$, $Z_1=2$—F, $Z_2=5$—F
Crystals (isopropanol); m.p.=129°-130° C.; yield 76%.

EXAMPLE 22

2-(3-Methoxyphenyl)aminonicotinaldehyde

Formula (VI): $X=Z_2=H$, $Z_1=3$—$OCH_3$
Crystals (isopropyl ether); m.p.=65°-66° C.; yield 75%.

EXAMPLE 23

2-(3-Chlorophenyl)aminonicotinaldehyde

Formula (VI): $X=Z_2=H$, $Z_1=3$—Cl
Crystals; m.p.=99°-100° C.; yield 78%.

EXAMPLE 24

2-(3-Nitrophenyl)aminonicotinaldehyde

Formula (VI): $X=Z_2=H$, $Z_1=3$—$NO_2$
Crystals (acetonitrile); m.p.=160°-162° C.; yield 70%.

EXAMPLE 25

2-(3-Methylphenyl)aminonicotinaldehyde

Formula (VI): $X=Z_2=H$, $Z_1=3$—$CH_3$
Crystals (isopropyl ether); m.p.=95°-97° C.; yield 79%.

EXAMPLE 26

2-(3-Cyano-4-chlorophenyl)aminonicotinaldehyde

Formula (VI): $X=H$, $Z_1=3$—CN, $Z_2=4$—Cl
Crystals (acetonitrile); m.p.=203° C.; yield 60%.

EXAMPLE 27

2-(3-Cyano-4-fluorophenyl)aminonicotinaldehyde

Formula (VI): $X=H$, $Z_1=3$—CN, $Z_2=4$—F
Crystals (acetonitrile); m.p.=193° C.; yield 80%.

EXAMPLE 28

2-(4-Chlorophenyl)aminonicotinaldehyde

Formula (VI): $X=Z_2=H$, $Z_1=4$—Cl

Crystals (isopropyl acetate); m.p.=101°-102° C.; yield 60%.

EXAMPLE 29

2-(3,5-Dichlorophenyl)aminonicotinaldehyde

Formula (VI): $X=H$, $Z_1=3$—Cl, $Z_2=5$—Cl
Crystals; m.p.=159° C.; yield 92%.

EXAMPLE 30

2-(4-Methoxyphenyl)aminonicotinaldehyde

Formula (VI): $X=Z_2=H$, $Z_1=4$—$OCH_3$
Crystals; m.p.=84° C.; yield 54%.

EXAMPLE 31

1-(3,5-Dichlorophenyl)-1,2-dihydro-3-dimethoxymethyl-2-oxo-1,8-naphthyridine

Formula (VIII): $X=H$, $R'=CH_3$, $Y'=O$, $Z_1=3$—Cl, $Z_2=5$—Cl

A solution of 42.7 g of 2-(3,5-dichlorophenyl)aminonicotinaldehyde, prepared in Example 29, in 500 ml of tetrahydrofuran containing 35.6 g of methyl 3,3-dimethoxypropionate, and a solution of sodium methylate prepared from 5.5 g of sodium in 100 ml of methanol, are stirred for 24 h at room temperature. The reaction mixture is subsequently concentrated under vacuum, water is then added and the crystals formed are filtered off, washed carefully with water and dried to give 44.25 g of 1-(3,5-dichlorophenyl)-1,2-dihydro-3-dimethoxymethyl-2-oxo-1,8-naphthyridine in the form of white crystals melting at 190° C. Yield 75.7%.

EXAMPLE 32

1,2-Dihydro-3-dimethoxymethyl-1-(4-methoxyphenyl)-2-oxo-1,8-naphthyridine

Formula (VIII): X $Z_2=H$, $R'=CH_3$, $Y'=O$, $Z_1=4$—$OCH_3$

The procedure of Example 31 using 20 g of 2-(4-methoxyphenyl)aminonicotinaldehyde, prepared in Example 30, gives, after recrystallization from methanol, 16.73 g of 1,2-dihydro-3-dimethoxymethyl-1-(4-methoxyphenyl)-2-oxo-1,8-naphthyridine in the form of white crystals melting at 210° C. Yield 58%.

EXAMPLE 33

1,2-Dihydro-3-dimethoxymethyl-2-imino-1-(4-methoxyphenyl)-1,8-naphthyridine

Formula (VIII): $X=Z_2=H$, $R'=CH_3$, $Y'=NH$, $Z_1=4$—$OCH_3$

The procedure of Example 31 using 14.6 g of 2-(4-methoxyphenylamino)nicotinaldehyde and 11.15 g of 3,3-dimethoxypropionitrile (1.5 eq) gives, after washing of the resulting solid with ether, 10.5 g of 1,2-dihydro-3-dimethoxymethyl-2-imino-1-(4-methoxyphenyl)-1,8-naphthyridine in the form of an off-white solid melting at 167° C. Yield 50.6%.

EXAMPLE 34

[1-(3,5-Dichlorophenyl)-1,2-dihydro-2-oxo-1,8-naphthyridin-3-yl]carboxaldehyde

Formula ( IX ): $X=H$, $Y'=O$, $Z_1=3$—Cl, $Z_2=5$—Cl

A suspension of 44.25 g of 1-(3,5-dichloro-phenyl)-1,2-dihydro-3-dimethoxymethyl-1,8-naphthyridine, prepared in Example 31, in 450 ml of tetrahydrofuran and 66 ml of 10% aqueous hydrochloric acid (1.5 eq) is stirred at room temperature. The solid passes into solution and then a precipitate forms. After 24 h, the reaction mixture is concentrated under vacuum and the residue obtained is taken up in dichloromethane; the organic phase is washed with 10% sodium bicarbonate and then water and dried over magnesium sulfate. After concentration under vacuum, the solid obtained is taken up in ether and filtered off to give 35.3 g of [1-(3,5-dichlorophenyl)-1,2-dihydro-2-oxo-1,8-naphthyridin-3-yl]carboxaldehyde melting at 250° C. Yield 91%.

EXAMPLE 35

[1,2-Dihydro-1-(4-methoxyphenyl)-2-oxo-1,8-naphthyridin-3-yl]carboxaldehyde

Formula ( IX ): $X=Z_2=H$, $Y'=O$, $Z_1=4$—$OCH_3$

The procedure of the previous Example using 16.73 g of 1,2-dihydro-3-dimethoxymethyl-1-(4-methoxyphenyl)-2-oxo-1,8-naphthyridine, prepared in Example 32, gives 13.8 g of [1,2-dihydro-1-(4-methoxyphenyl)-2-oxo-1,8-naphthyridin-3-yl]carboxaldehyde melting at 245° C. Yield 95%.

EXAMPLE 36

[1,2-Dihydro-2-imino-1-(4-methoxyphenyl)-1,8-naphthyridin-3-yl]carboxaldehyde hydrochloride Formula ( IX ): $X=Z_2=H$, $Z_1=4$—$OCH_3$, $Y'=NH$ 10.9 g of 1,2-dihydro-3-dimethoxymethyl-2-imino-1-(4-methoxyphenyl)-1,8-naphthyridine, prepared in Example 33, are suspended in 110 ml of tetrahydrofuran and the suspension is stirred. After the addition of 18.5 ml of 10% aqueous hydrochloric acid (1.5 eq), the solid passes into solution and then a precipitate is gradually observed. After 8 h, the solid is filtered off and washed with a small amount of tetrahydrofuran.

This gives 7.6 g of [1,2-dihydro-2-imino-1-(4-methoxyphenyl)-1,8-naphthyridin-3-yl]carboxaldehyde hydrochloride in the form of a pale yellow solid melting at 170° C. Yield 72%.

EXAMPLE 37

3-[1-(3,5-Dichlorophenyl)-1,2-dihydro-2-oxo-1,8-naphthyridin-3-yl]-3-hydroxy-2-(3-pyridyl)propionitrile Formula (XII): $X=H$, $Y'=O$, $Z_1=3$—Cl, $Z_2=5$—Cl, R=3-pyridyl 5.7 g of [1-(3,5-dichlorophenyl)-1,2-dihydro-2-oxo-1,8-naphthyridin-3-yl]carboxaldehyde are suspended in 60 ml of ethanol with 2.33 ml of 3-pyridylacetonitrile (1.2 eq) and a few drops of piperidine. The medium is refluxed for 4 h and then cooled. The solid formed is filtered off and washed with ethanol to give 7.2 g of 3-[1-(3,5-dichlorophenyl)-1,2-dihydro-2-oxo-1,8-naphthyridin-3-yl]-3-hydroxy-2-(3-pyridyl)propionitrile in the form of a white solid melting at 260° C. Yield 91%.

EXAMPLE 38

3-[1-(3,5-Dichlorophenyl)-1,2-dihydro-2-oxo-1,8-naphthyridin-3-yl]-2-(3-pyridyl)prop-2-enenitrile Formula (I): $X=H$, $Y=O$, $Z_1=3$—Cl, $Z_2=5$—Cl, R=3-pyridyl 3 g of 3-[1-(3,5-dichlorophenyl)-1,2-dihydro-2-oxo-1,8-naphthyridin-3-yl]-3-hydroxy-2-(3-pyridyl)propionitrile are suspended in 20 ml of dichloromethane.

After the addition of 1.05 ml of trifluoroacetic acid (2 eq), a yellow solution is obtained which becomes bright yellow with a rise in temperature after the addition of 1.44 ml of trifluoroacetic anhydride (1.5 eq). This solution is stirred for one hour and water is then added; the organic phase is decanted, washed with a 10% solution of sodium bicarbonate and then water and dried over magnesium sulfate. After concentration under vacuum, the solid obtained is washed with ether and dried to give 2.6 g of 3-[1-(3,5-dichlorophenyl)-1,2-dihydro-2-oxo-1,8-naphthyridin-3-yl]-2-(3-pyridyl)prop-2-enenitrile in the form of a bright yellow solid melting at 261° C. Yield 91%.

EXAMPLE 39

3-[1-(3,5-Dichlorophenyl)-1,2-dihydro-2-oxo-1,8-naphthyridin-3-yl]-2-(2-pyridyl)prop-2-enenitrile Formula (I): $X=H$, $Y=O$, $Z_1=3$—Cl, $Z_2=5$—Cl, $R=2$-pyridyl 3.2 g of [1-(3,5-dichlorophenyl)-1,2-dihydro-2-oxo-1,8-naphthyridin-3-yl]carboxaldehyde, prepared in Example 34, are refluxed in 30 ml of ethanol with 1.4 ml of 2-pyridylacetonitrile (1.2 eq) and a few drops of piperidine.

After refluxing for 3 h, the reaction mixture is cooled and the bright yellow precipitate formed is filtered off and washed with ethanol to give 3.77 g of 3-[1-(3,5-dichlorophenyl)-1,2-dihydro-2-oxo-1,8-naphthyridin-3-yl]-2-(2-pyridyl)prop-2-enenitrile in the form of bright yellow crystals after purification by chromatography on a silica column (eluent: dichloromethane). Melting point 319° C. Yield 70%.

EXAMPLE 40

3-[1,2-Dihydro-1-(4-methoxyphenyl)-2-oxo-1,8-naphthyridin-3-yl]-2-(4-pyridyl)prop-2-enenitrile Formula (I): $X=Z_2=H$, $Y=O$, $Z_1=4$—$OCH_3$, $R=4$-pyridyl 2.8 g of [1,2-dihydro-1-(4-methoxyphenyl)-2-oxo-1,8-naphthyridin-3-yl]carboxaldehyde, prepared in Example 35, are added to a suspension of 1.6 g of 4-pyridylacetonitrile hydrochloride (1 eq) in 80 ml of ethanol containing 0.253 g of sodium (1.1 eq). The reaction mixture is refluxed for 3 h and then cooled to room temperature. The solid formed is filtered off, washed with ethanol and water and then recrystalilzed from methoxyethanol to give 1.3 g of 3-[1,2-dihydro-1-(4-methoxyphenyl)-2-oxo-1,8-naphthyridin-3-yl]-2-(4-pyridyl)prop-2-enenitrile in the form of bright yellow crystals melting at 283° C. Yield 34.5%.

EXAMPLE 41

3-[1-(3,5-Dichlorophenyl)-1,2-dihydro-2-oxo-1,8-naphthyridin-3-yl]-2-(4-pyridyl)prop-2-enenitrile Formula (I): $X=H$, $Y=O$, $Z_1=3$—Cl, $Z_2=5$—Cl, $R=4$-pyridyl The procedure of Example 40 using 3.2 g of [1-(3,5-dichlorophenyl)-1,2-dihydro-2-oxo-1,8-naphthyridin-3-yl]carboxaldehyde gives, after recrystallization from methoxyethanol, 1.68 g of 3-[1-(3,5-dichlorophenyl)-1,2-dihydro-2-oxo-1,8-naphthyridin-3-yl]-2-(4-pyridyl)prop-2-enenitrile in the form of a bright yellow solid melting at 256°–257° C. Yield 40%.

EXAMPLE 42

3-[1,2-Dihydro-1-(4-methoxyphenyl)-2-oxo-1,8-naphthyridin-3-yl]-2-(3-pyridyl)prop-2-enenitrile Formula (I): $X=Z_2=H$, $Y=O$, $Z_1=4$—$OCH_3$, $R=3$-pyridyl The procedure of Example 39 using 2.8 g of [1,2-dihydro-1-(4-methoxyphenyl)-2-oxo-1,8-naphthyridin-3-yl]carboxaldehyde and 1.3 ml of 3-pyridylacetonitrile (1.2 eq) gives 2.5 g of a yellow solid, which is purified by chromatography on a silica column (eluent: dichloromethane/ethyl ether 9/1).

This gives 1.5 g of 3-[1,2-dihydro-1-(4-methoxyphenyl)-2-oxo-1,8-naphthyridin-3-yl]-2-(3-pyridyl)-prop-2-enenitrile in the form of a bright yellow solid melting at 244° C. Yield 40%.

EXAMPLE 43

3-[1,2-Dihydro-1-(4-methoxyphenyl)-2-oxo-1,8-naphthyridin-3-yl]-2-(2-pyridyl)prop-2-enenitrile Formula (I): $X=Z_2=H$, $Y=O$, $Z_1=4$—$OCH_3$, $R=2$-pyridyl 2.8 g of [1,2-dihydro-1-(4-methoxyphenyl)-2-oxo-1,8-naphthyridin-3-yl]carboxaldehyde are suspended in 90 ml of ethanol with 1.2 ml of 2-pyridylacetonitrile (1.1 eq). A solution of 0.023 g of sodium in 10 ml of ethanol (0.1 eq) is then added. The pale yellow suspension obtained is stirred for 24 h and gradually becomes bright yellow. The precipitate formed is filtered off and washed with ethanol and then ether to give 3.4 g of 3-[1,2-dihydro-1-(4-methoxyphenyl)-2-oxo-1,8-naphthyridin-3-yl]-2-(2-pyridyl)prop-2-enenitrile in the form of an orange-yellow solid melting at 251° C. Yield 89.5%.

EXAMPLE 44

3-[1-(3,5-Dichlorophenyl)-1,2-dihydro-2-thioxo-1,8-naphthyridin-3-yl]-2-(3-pyridyl)prop-2-enenitrile Formula (I): $X=H$, $Y=S$, $Z_1=3$—Cl, $Z_2=5$—Cl, $R=3$-pyridyl 0.9 g of 3-[1-(3,5-dichlorophenyl)-1,2-dihydro-2-oxo-1,8-naphthyridin-3-yl]-2-(3-pyridyl)prop-2-enenitrile is refluxed in 15 ml of xylene with 0.23 g of phosphorus pentasulfide for 8 hours.

The medium is filtered hot and the filtrate is cooled to room temperature. The precipitate formed is filtered off and washed with ether.

This gives 0.1 g of 3-[1-(3,5-dichlorophenyl)-1,2-dihydro-2-thioxo-1,8-naphthyridin-3-yl]-2-(3-pyridyl)prop-2-enenitrile in the form of an orange solid melting at 260°–261° C. Yield 10%.

PHARMACOLOGY

Measurement of inhibition of the cell proliferation induced by a growth factor in rat aorta smooth muscle cells I. Principle Inhibition of the cell proliferation induced by a growth factor (for example PDGF) is evaluated by measuring the incorporation of $^3$H-thymidine into rat aorta smooth muscle cells (VSMC).

II. Procedure

The VSMC are cultivated at 37° C. with 5% of $CO_2$ up to the point of subconfluence and are then placed for 24 hours under rest conditions in a serum-impoverished medium. They are subsequently pretreated for one hour with the test molecule ($10^{-5}M$) and then stimulated for 22 hours with a growth factor (for example PDGF). $^3$H-Thymidine is incorporated over the last 2 hours. All these steps are performed at 37° C. with 5% of $CO_2$.

The reaction is terminated by sucking off the reaction medium, detaching the cells and then filtering the lyzed cells through glass fiber filters.

III. Expression of the results

The results are expressed as the percentage inhibition of the stimulation of $^3$H-thymidine incorporation due to the action of the growth factor.

The results obtained show that the compounds of formula (I), and in particular the product of Example 38, exert a powerful inhibition of the proliferation of smooth muscle cells stimulated by PDGF.

| Product of | % inhibition of the incorporation of $^3$H-thymidine stimulated by PDGF | |
|---|---|---|
| | 1E - 5M | 1E - 6M |
| Example 38 | 100 | 100 |

TOXICOLOGY

Preliminary studies have demonstrated the good tolerance of the compounds of formula (I), in particular the compound of Example 38, up to a dose of 300 mg/kg, administered intraperitoneally and orally to rats.

What is claimed is:

1. A naphthyridine compound of formula (I):

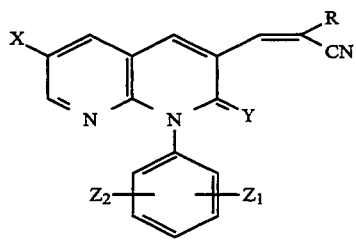

Formula (I)

in which:

X is:
- the hydrogen atom,
- a halogen atom,
- an OH radical or
- a lower O-alkyl radical having 1 to 6 carbon atoms;

Y is:
- the oxygen atom,
- the sulfur atom or
- an NH Group;

$Z_1$ and $Z_2$ are independently:
- the hydrogen atom,
- a lower alkyl radical having 1 to 6 carbon atoms,
- a halogen atom,
- a trifluoromethyl radical,
- an OH radical,
- a lower O-alkyl radical having 1 to 6 carbon atoms,
- a lower S-alkyl radical having 1 to 6 carbon atoms,
- an $NO_2$ radical or
- a CN radical, or $Z_1$ and $Z_2$ together form a methylenedioxy group; and R is:
- a pyridine ring,
- an imidazole ring,
- an indole ring,
- a group —$CONH_2$ or —$CSNH_2$,
- a group

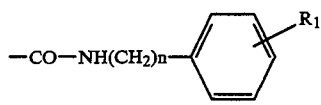

in which n is an integer from 0 to 5 and $R_1$ is the hydrogen atom or a halogen atom, or
- a group $COOR_2$, $R_2$ being a lower alkyl radical having 1 to 6 carbon atoms, and its addition salts.

2. A compound of formula (I) according to claim 1 wherein:

X is:
- the hydrogen atom;

Y is:
- the oxygen atom or
- the sulfur atom;

$Z_1$ and $Z_2$ are independently:
- the hydrogen atom,
- the chlorine atom or
- a lower O-alkyl radical having 1 to 6 carbon atoms; and R is:
- a pyridine ring, and its addition salts.

3. A compound according to claim 1 wherein X is the hydrogen atom.

4. A compound according to claim 1 wherein Y is the oxygen atom or the sulfur atom.

5. A compound according to claim 1 wherein $Z_1$ and $Z_2$ are a chlorine atom, one in the 3-position and the other in the 5-position, or wherein $Z_1$ is a methoxy group in the 4-position and $Z_2$ is a hydrogen atom.

6. A compound according to claim 1 which is the compound of the formula 3-[1-(3,5-dichlorophenyl)-1,2-dihydro-2-oxo-1,8-naphthyridin-3-yl]-2-(3-pyridyl)-prop-2-enenitrile:

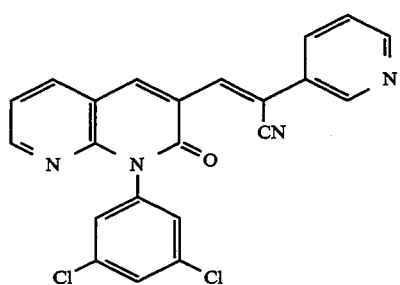

7. A compound according to claim 1 which is selected from the derivatives of the formulae 3-[1-(3,5-dichlorophenyl)-1,2-dihydro-2-oxo-1,8-naphthyridin-3-yl]-2-(2-pyridyl)prop-2-enenitrile:

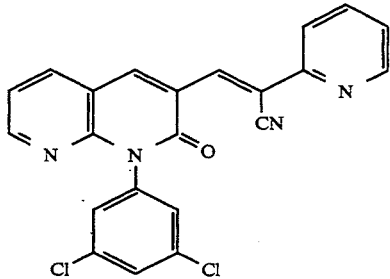

3-[1-(3,5-dichlorophenyl)-1,2-dihydro-2-thioxo-1,8-naphthyridin-3-yl]-2-(3-pyridyl)prop-2-enenitrile:

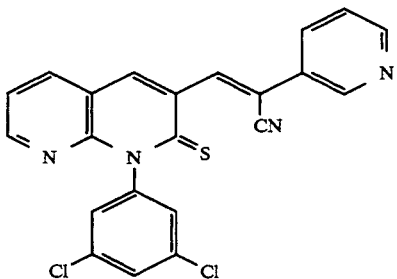

3-[1,2-dihydro-1-(4-methoxyphenyl)-2-oxo-1,8-naphthyridin-3-yl]-2-(4-pyridyl)prop-2-enenitrile:

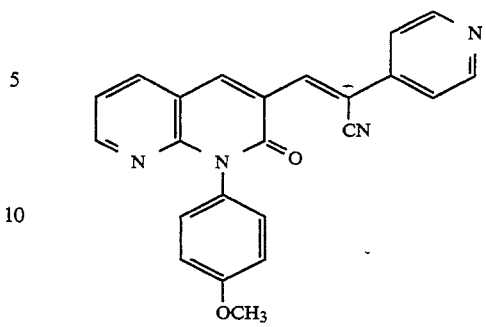

8. A pharmaceutical composition which comprises a pharmaceutically effective amount of at least one compound of formula (I) as defined in claim 1, or one of its pharmaceutically acceptable addition salts, incorporated in a pharmaceutically acceptable excipient, vehicle or carrier.

9. A pharmaceutical composition, active in treatment of atherosclerosis or restenosis induced by smooth muscle cell proliferation which contains a pharmaceutically effective amount of at least one compound of formula (I) as defined in claim 1, or one of its pharmaceutically acceptable addition salts, incorporated in a pharmaceutically acceptable excipient, vehicle or carrier.

10. A pharmaceutical composition, according to claim 8, which is formulated as gelatin capsules or tablets containing from 1 mg to 1000 mg of active ingredient, or as injectable preparations containing from 0.1 to 500 mg of active ingredient.

11. A method of therapeutic treatment of atherosclerosis or restenosis induced by smooth muscle cell proliferation for mammals, which comprises administering to this mammal a therapeutic effective amount of at least one compound of formula (I) as defined in claim 1, or one of its pharmaceutically acceptable addition salts.

* * * * *